(12) United States Patent
Wang et al.

(10) Patent No.: US 9,687,499 B2
(45) Date of Patent: Jun. 27, 2017

(54) METHOD USING HEAT SHOCK PROTEIN INHIBITOR FOR TREATING HEPATITIS AND HEPATOMA

(71) Applicant: National Tsing Hua University, Hsinchu (TW)

(72) Inventors: Hui-Ching Wang, Hsinchu (TW); Ting-Chung Yen, Hsinchu (TW); Li-Rung Huang, Hsinchu (TW)

(73) Assignee: National Tsing Hua University

( * ) Notice: Subject to any disclaimer, the term of this patent is extended or adjusted under 35 U.S.C. 154(b) by 0 days.

(21) Appl. No.: 14/749,091

(22) Filed: Jun. 24, 2015

(65) Prior Publication Data

US 2015/0366892 A1 Dec. 24, 2015

(30) Foreign Application Priority Data

Jun. 24, 2014 (TW) .............................. 103121657 A

(51) Int. Cl.
| *A01N 43/04* | (2006.01) |
| *A61K 31/70* | (2006.01) |
| *A61K 31/7076* | (2006.01) |
| *A61K 31/18* | (2006.01) |
| *A61K 31/706* | (2006.01) |
| *A61K 31/7064* | (2006.01) |

(52) U.S. Cl.
CPC .......... *A61K 31/7076* (2013.01); *A61K 31/18* (2013.01); *A61K 31/706* (2013.01); *A61K 31/7064* (2013.01)

(58) Field of Classification Search
None
See application file for complete search history.

(56) References Cited

PUBLICATIONS

Leu et al. Molecular Cell (2009), vol. 36, pp. 15-27.*
Macias et al. Journal of Medicinal Chemistry (2010), vol. 54, pp. 4034-4041.*
Williamson et al. J. Med. Chem. (2009), vol. 52, pp. 1510-1513.*

* cited by examiner

*Primary Examiner* — Patrick Lewis
(74) *Attorney, Agent, or Firm* — Muncy, Geissler, Olds & Lowe, P.C.

(57) ABSTRACT

The present invention is directed to a use of a heat shock protein inhibitor in preparing pharmaceutical composition for treating hepatitis by scavenging hepatitis B virus-infected cells. The heat shock protein inhibitor is selected from a group including VER-155008, Pifithrin-μ, and pharmaceutical acceptable salts thereof. The present invention is also directed to a use of a heat shock protein inhibitor in preparing pharmaceutical composition for treating hepatoma.

10 Claims, 6 Drawing Sheets
(1 of 6 Drawing Sheet(s) Filed in Color)

Mock     VER-155008 20 mg/Kg     Pifithrin-μ 20 mg/Kg

METHOD USING HEAT SHOCK PROTEIN INHIBITOR FOR TREATING HEPATITIS AND HEPATOMA

BACKGROUND OF THE INVENTION

1. Field of the Invention

The present invention relates to a method for treating hepatitis B or hepatoma, particularly to a method using heat shock protein inhibitor for treating hepatitis B or hepatoma.

2. Description of the Prior Art

Hepatitis is the national disease of Taiwan. Until now, the prevalence rate of hepatitis B is still as high as 16% in Taiwan, which is the highest one in the world. Traditionally, liver disease is a native disease prevailing in Asia. Hepatoma is a cancer frequently seen in Taiwan, mainland China, Thailand and Korea. Hepatocellular carcinoma is often seen in Asia and Africa. In spite of being treated with surgery, chemotherapy or radiotherapy, the patients suffering hepatocellular carcinoma still have low average survival rate. According to epidemiological study, the regions of high hepatitis virus infection rate have more hepatoma cases. In Taiwan, over 90% of the patients of hepatoma are the carriers of hepatitis B virus.

After infecting a patient, hepatitis B virus will reproduce massively in the liver of the patient. At present, the medication to treat hepatitis B includes the hypodermic injection-type interferon-group drugs and the oral-type nucleoside-group drugs, such as Zeffix (Lamivudine), He-psera (Adefovir Dipivoxil), Baraclude (Entecavir), Sebivo (Telbivudine), and Viread (Tenofovir). However, the abovementioned drugs are unable to scavenge hepatitis B virus but only to inhibit the reproduction of hepatitis B virus in the liver. Therefore, hepatitis B is still hard to be radically cured at present. Hence, it is necessary to develop a drug able to thoroughly scavenge hepatitis B virus-infected cells.

SUMMARY OF THE INVENTION

One objective of the present invention is to provide a drug for treating or controlling hepatitis B, which can scavenge the cells infected by hepatitis B virus.

In one embodiment, the present invention proposes a method using heat shock protein inhibitor for treating or controlling hepatitis B, wherein the heat shock protein inhibitor comprises VER-155008, Pifithrin-µ, or the pharmaceutical acceptable salts thereof.

Another objective of the present invention is to provide a method for treating hepatoma, which can scavenge the cells infected by hepatitis B virus.

In another embodiment, the present invention proposes a method using heat shock protein inhibitor for treating hepatoma, wherein the heat shock protein inhibitor comprises VER-155008, Pifithrin-µ, or the pharmaceutical acceptable salts thereof.

The embodiments of the present invention will be described in detail in cooperation with the attached drawings to make easily understood the aspects, characteristics and advantages of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF THE PREFERRED EMBODIMENT

The present invention discloses a use of a heat shock protein inhibitor in preparing a pharmaceutical composition for treating or controlling hepatitis B, wherein the heat shock protein inhibitor comprises VER-155008, Pifithrin-µ, or the pharmaceutical acceptable salts thereof.

The chemical name of VER-155008 is 5'-O-[(4-Cyanophenyl)methyl]-8-[[(3,4-dichlorophenyl)methyl]amino]-adenosine. VER-155008 is an effective HSP70 family inhibitor, having 1050 of 0.5 µM and 2.6 µM to HSP70 and GRP78. The effect of VER-155008 to HSP70 and GRP78 is over 100 times higher than its effect to HSP90. The representative structural formula of VER-155008 is expressed by

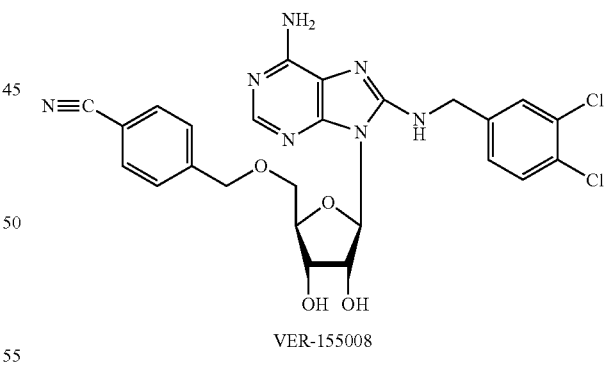

VER-155008

The chemical name of Pifithrin-µ is 2-Phenylethynesulfonamide. Pifithrin-µ is a p53-specific inhibitor, decreasing the affinity of p53 to Bcl-xL and Bcl-2 and inhibiting the function of HPS70 and autophagy. Both VER-155008 and Pifithrin-µ are commercially available in the market, such as Sigma SML0271 and Sigma P0122. However, it should be noted: the heat shock protein inhibitor mentioned in the present invention is not limited to the commercially-available VER-155008 and Pifithrin-µ but also includes the compounds obtained by chemical synthesis. The representative structural formula of Pifithrin-µ is expressed by

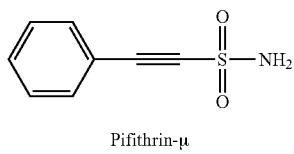 [SMILES: NS(=O)(=O)C#Cc1ccccc1]

Pifithrin-μ

A US patent No. US20110189125 disclosed a use of Pifithrin-μ in treating tumor cells, which causes plasmolysis, protein aggregation, peel-off from the substrate, and autophagy. The prior art also disclosed that tumor cells are more sensitive to the cytotoxicity of Pifithrin-μ than normal cells. However, no prior art has disclosed the use of Pifithrin-μ in treating hepatitis B and hepatoma so far.

Figure 1:
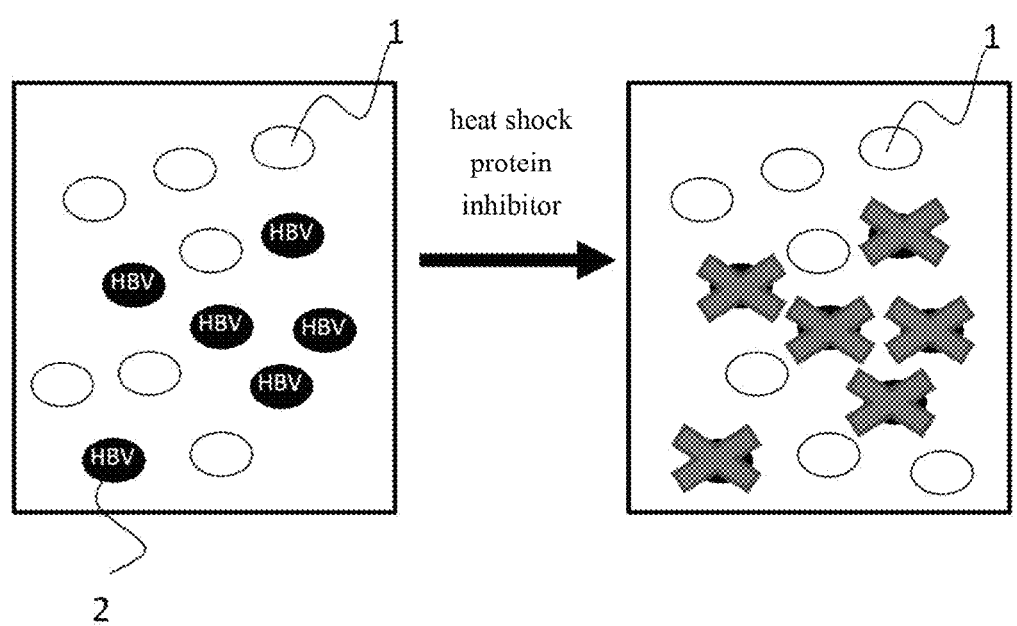
FIG. 1 is a diagram schematically showing a use of a heat shock protein inhibitor to scavenge HBV-infected cells of chronic hepatitis B according to one embodiment of the present invention.

Refer to FIG. 1 a diagram schematically showing a novel use of a heat shock protein inhibitor to scavenge HBV-infected cells of chronic hepatitis B according to one embodiment of the present invention, wherein "1" designates normal cells and "2" designates HBV-infected cells. The heat shock protein inhibitors of the present invention are able to modulate specific heat shock proteins and cytotoxically kill the HBV-infected liver cells specifically. Among heat shock protein inhibitors, VER-155008 can inhibit HSC70, GRP78 and HSP90; Pifithrin-μ can inhibit HSP72. It has been found: VER-155008 and Pifithrin-μ can specifically kill the virus-infected liver cells and reduce the viral load in mice. Therefore, VER-155008 and Pifithrin-μ can be clinically applied to treating hepatitis B. The gene of hepatitis B virus and the proteins expressed by hepatitis B virus are regarded as important carcinogenic factors. In other words, infection by hepatitis virus may lead to hepatoma. In Taiwan, a very high percentage of the patients of hepatoma carry hepatitis B virus. The present invention can scavenge the virus of chronic hepatitis B and thus can treat hepatoma. In one embodiment, the present invention can treat hepatoma caused by hepatitis. In one embodiment, hepatoma is caused by hepatitis B virus. As Pifithrin-μ can selectively inhibit carcinoma, the heat shock protein inhibitor of the present invention can apply to cancer treatment.

In the present invention, the term "control" means "limit the viral load in a controllable range especially in an undetectable range".

The heat shock protein inhibitor can be in form of a corresponding salt, ester or prodrug. The "pharmaceutical acceptable salts" mentioned in the specification are referred to the salts or amphoteric ions of the compounds of the present invention. The salts of the compounds are prepared via letting the compound react with an acid having an appropriate cation in the final separation or purification process of the reaction or fabricated or in an independent process. The cations meeting the requirement of pharmacy include the cations of the alkali group (such as sodium or potassium) and the cations of the alkaline earth group (such as calcium or magnesium). For the alkaline-centered compounds of the present invention, the pharmaceutical acceptable salts thereof are the acid addition salts of the pharmaceutical acceptable acids, including inorganic acids (such as hydrochloric acid, hydrobromic acid, sulfuric acid, and phosphoric acid) and organic acids (such as oxalic acid, maleic acid, succinic acid, malonic acid, lactic acid and citric acid). The compounds of the present invention include the compounds disclosed in the specification, the pharmaceutical acceptable salts thereof, the pharmaceutical solvates thereof (such as the hydrates thereof), the pharmaceutical esters thereof, and the prodrugs thereof. As both VER-155008 and Pifithrin-μ have amino groups, they can react with acid to form pharmaceutical acceptable salts.

In the present invention, pharmaceutical acceptable carriers are mixed with the pharmaceutical compositions for preparing appropriate dosage and appropriate dosage forms according to the conventional medicine formulation technology. In the present invention, the pharmaceutical acceptable carriers are familiar to the persons skilled in the art, used to prepare various dosage forms, such as tablets, capsules, gels, solutions, and suspensions. In the present invention, the pharmaceutical acceptable carriers include pharmaceutical excipients and pharmaceutical carrier agents, which are nontoxic and inertial solid-state materials, semi-solid materials, diluents, encapsulants, gel bases, or formulation adjuvants, such as microcrystalline cellulose, glucose, skim milk powder, starch, silica, anhydrous calcium hydrogen phosphate, magnesium phosphate, stearic acid, magnesium stearate, or artificial flavors.

Below, embodiments are described in detail in cooperation with the attached drawings to demonstrate the objectives, technical contents, characteristics and accomplishments of the present invention and enable the persons skilled in the art to understand, make and use the present invention. However, it should be appreciated: the embodiments are only to exemplify the present invention but not to limit the scope of the present invention.

Figure 2A:
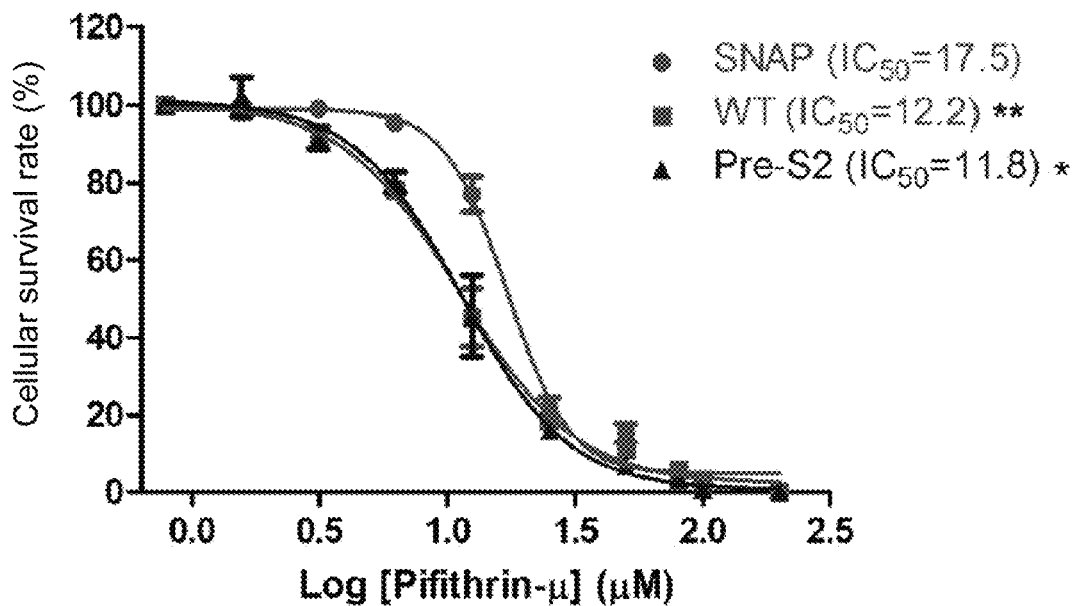
FIG. 2a and FIG. 2b show the toxicities of the heat shock protein inhibitors of the present invention to the parental liver cells according to the data obtained in experiments.
Figure 2B:
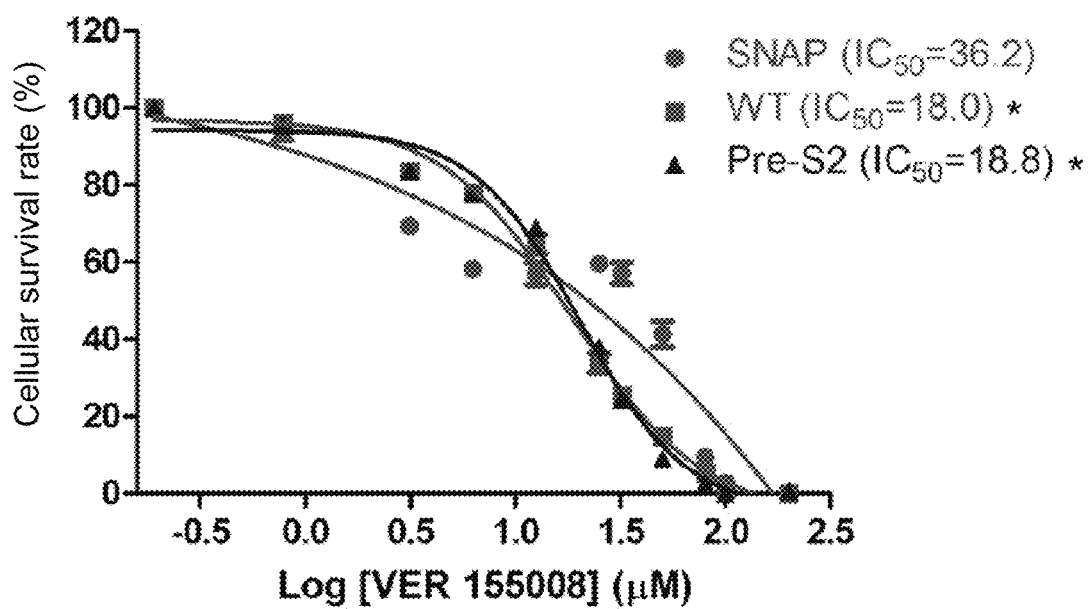

Toxicities of the Heat Shock Protein Inhibitor of the Present Invention to Liver Cells Refer to FIG. 2a and FIG. 2b. FIG. 2a shows that the 1050 of Pifithrin-μ to the parental liver cell lines SNAP, WT and Pre-S2 are respectively 17.5 μM, 12.2 μM and 11.8 μM. FIG. 2b shows that the 1050 of VER-155008 to the parental liver cell lines SNAP, WT and Pre-S2 are respectively 36.2 μM, 18.0 μM and 18.8 μM. The 1050 of Pifithrin-μ and VER-15500 are in the μM scale. Therefore, the toxicities of Pifithrin-μ and VER-15500 to liver cells are very low.

Selectivity to Kill Virus-Infected Liver Cells In-Vitro

Figure 3A:
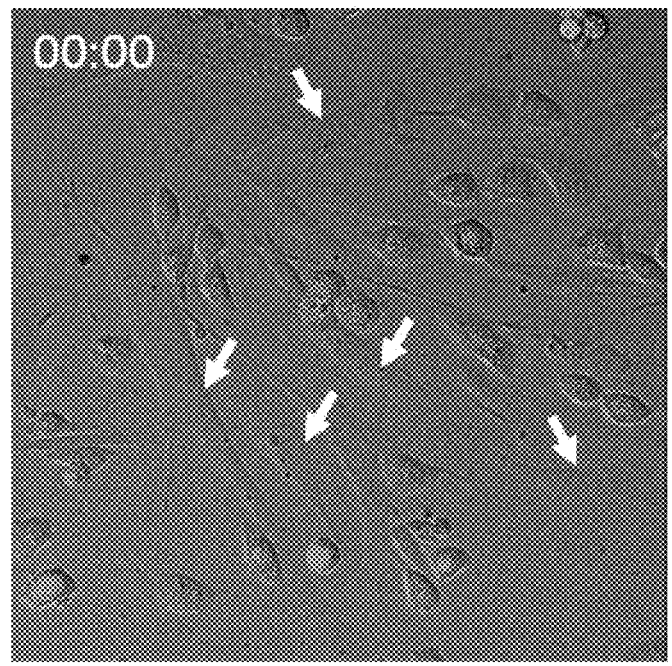
FIGS. 3a-3c show the selective cytotoxicity of the heat shock protein inhibitor of the present invention to the cells expressing HBV-LHBs according to the data obtained in experiments.
Figure 3B:
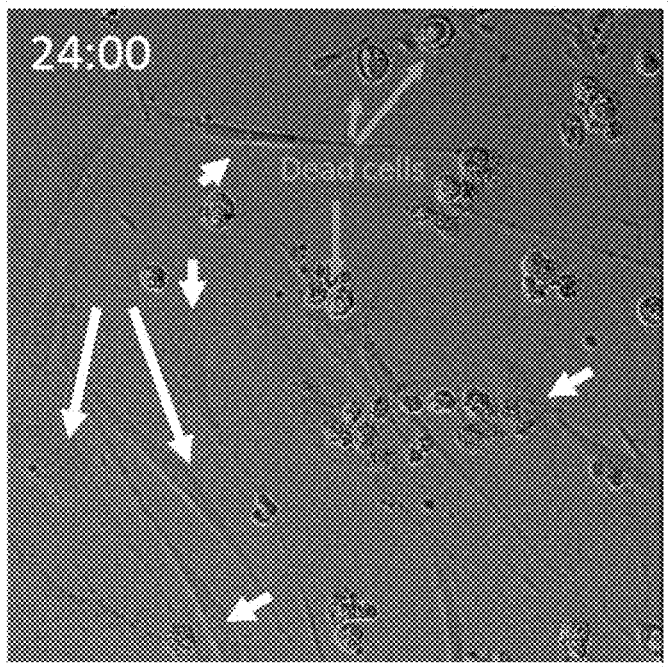
Figure 3C:
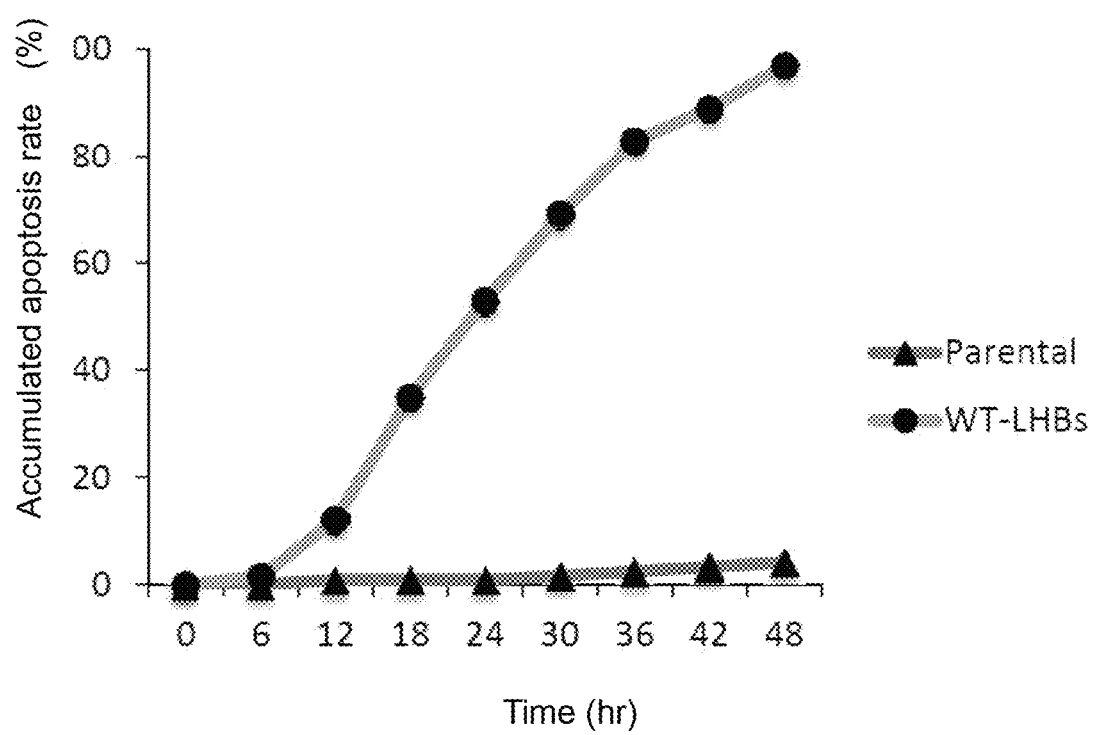

With elapse of time, use a microscope to observe the selective cytotoxicity of VER-155008 to the cells expressing HBV-LHBs (hepatitis B virus large S protein). The LHBs-positive cells (SNAP cells 505) are labeled by green fluorescence and co-cultured with unlabeled parental NeHep-LxHT. The group of the mixed cells is processed with 40 μM VER-155008 and then periodically recorded at time points separated by a longer interval of time for 48 hours. The observed cellular quantities of the unlabeled cells (parental cells) and the green-labeled cells (LHBs-infected cells) are used to reveal typical cellular apoptosis. FIG. 3a shows that the parental cells (indicated by the white arrows) and the LHBs-infected cells (green-labeled) are live before they are processed by VER-155008. FIG. 3b shows that many of the LHBs-positive cells are dead and the parental cells (indicated by the white arrows) are still alive after they have been processed by VER-155008 for 24 hours. FIG. 3c shows the relationships of apoptosis rates and time and shows that the LHBs-infected cells almost all die after they have been processed by VER-155008 for 48 hours.

Reduction of Hepatitis B Surface Antigen in the Blood Serum of Mice by VER-15500 and Pifithrin-μ

Figure 4A:
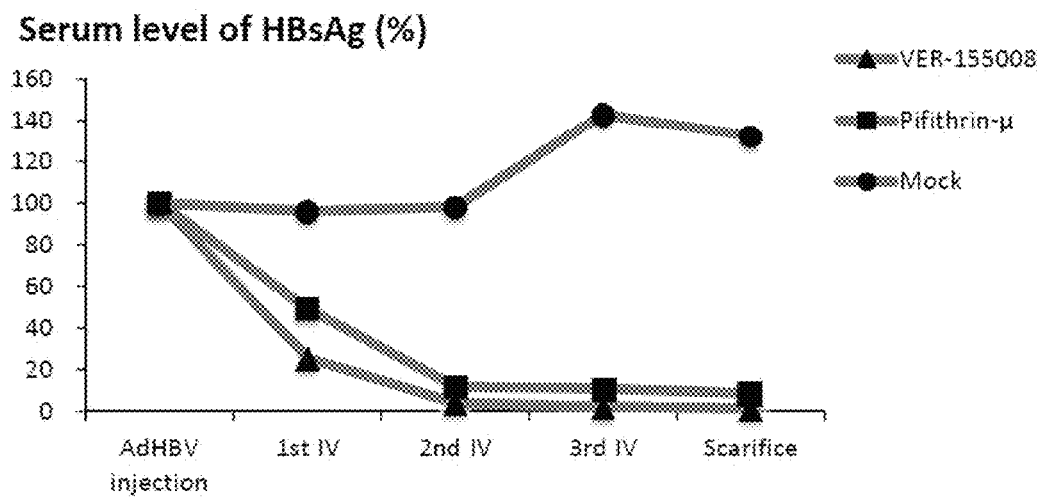
FIG. 4a shows the effects of the heat shock protein inhibitors of the present invention to the HBsAg expression level in the blood serum of mice according to the data obtained in experiments.

Intravenous injection of VER-15500 and Pifithrin-μ can successfully reduce the hepatitis B surface antigen (HBsAg) in the blood serum of mice, wherein the mice are continuously infected by hepatitis B virus in an adenovirus genome transfer technology (AdHBV). Each group has three mice. The experiment design is as follows: inject AdHBV into mice continuously for 28 days; respectively inject a mock medication, 20 mg/ml VER-15500, and 20 mg/ml Pifithrin-μ into the mice intravenously; collect the samples of the blood serum and livers for serological and pathological analyses. FIG. 4a shows that the blood serums of the mice, which are processed by a mock medication, VER-15500, and Pifithrin-μ, all express HBsAg and that the levels of HBsAg in the blood serums of the mice, which are processed by VER-15500 and Pifithrin-μ, are obviously reduced.

VER-15500 and Pifithrin-μ Processions and Liver Function Tests

Figure 4B:
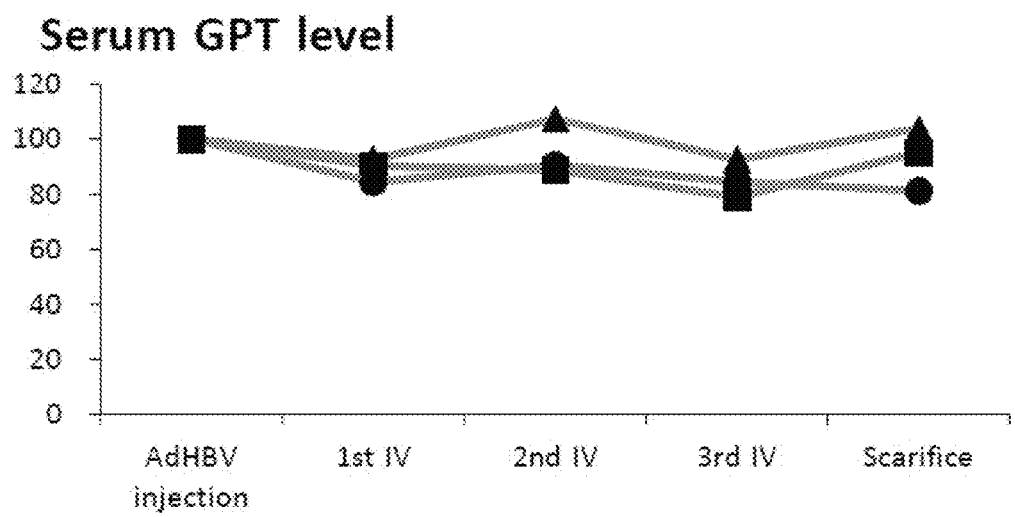
FIG. 4b shows the effects of the heat shock protein inhibitors of the present invention to the liver function of mice according to the data obtained in experiments.

GPT (Glutamate Pyruvate Transaminase) is used to monitor the liver function of the mice. FIG. 4b shows the levels of GPT in the blood serums do not vary obviously. It indicates that VER-15500 and Pifithrin-μ do not affect the liver function of the mice.

Figure 5A:
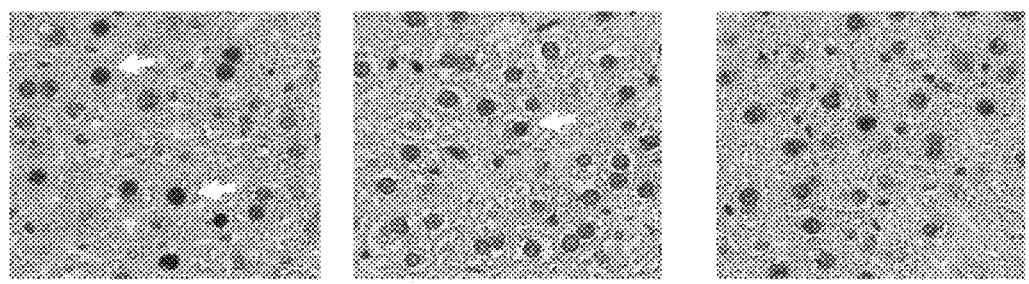
FIG. 5a and FIG. 5b show the effects to the quantities of the HBsAg-positive liver cells after the treatments by the heat shock protein inhibitors of the present invention according to the data obtained in experiments.
Figure 5B:
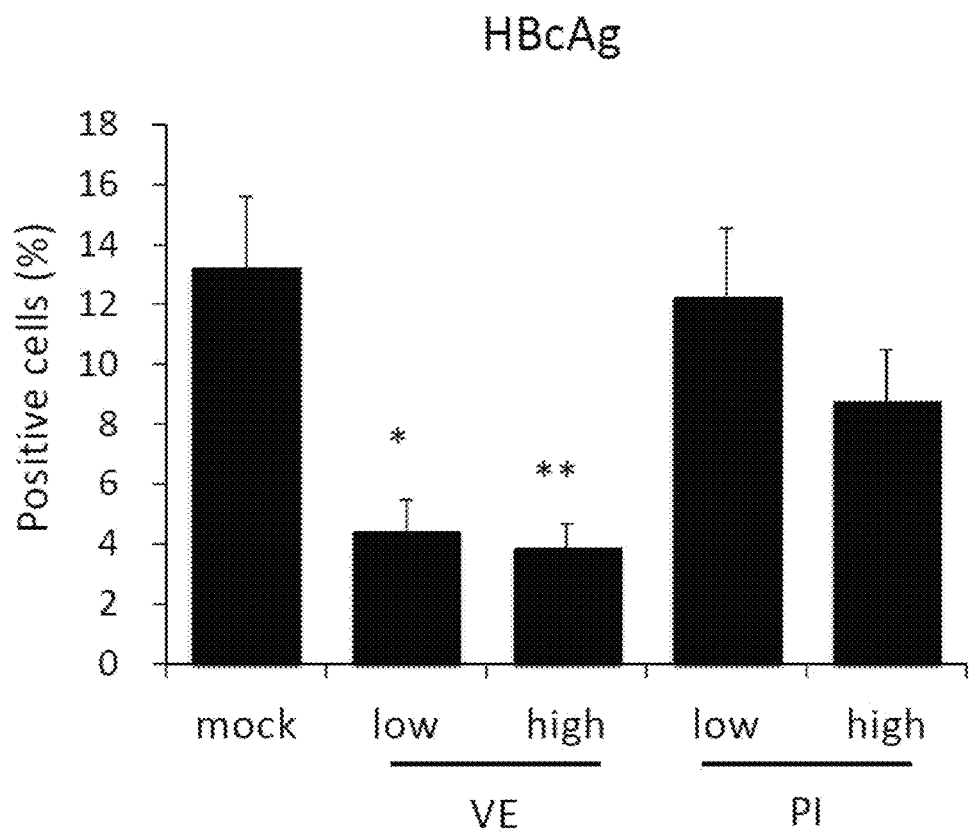

In the liver cells of the mice, the cells expressing HBV surface antigen (HBsAg) are obviously decreased after a month-long treatment. FIG. 5a shows the representative images of the liver sections dyed with HBsAg. FIG. 5b shows the percentages of the HBsAg-positive liver cells after the treatments with a low dosage (20 mg/Kg) of VER-15500 (VE) and Pifithrin-μ (PI) and a high dosage (40 mg/Kg) of VER-15500 (VE) and Pifithrin-μ (PI). The low dosage and high dosage of VER-15500 have different effects in decreasing the HBsAg-positive liver cells. The high dosage (40 mg/Kg) of Pifithrin-μ (PI) can also kill a portion of the HBcAg-positive liver cells. In FIG. 5b, * denotes P<0.05, and ** denotes P<0.01.

What is claimed is:

1. A method for treating hepatitis B, which comprises administering an effective amount of the pharmaceutical composition to a subject infected hepatitis with B virus;
    wherein the pharmaceutical composition comprises: 5'-O-[(4-Cyanophenyl)methyl]-8-[[(3,4-dichlorophenyl) methyl]amino]-adenosine (VER-155008), 2-Phenyl-ethynesulfonamide (Pifithrin-μ), or pharmaceutical acceptable salts thereof.

2. The method for treating hepatitis B according to claim 1, wherein said heat shock protein inhibitor is selected from a group consisting of VER-155008 and Pifithrin-μ.

3. The method for treating hepatitis B according to claim 1, wherein said heat shock protein inhibitor is VER-155008.

4. The method for treating hepatitis B according to claim 1, wherein said heat shock protein inhibitor is Pifithrin-μ.

5. The method for treating hepatitis B according to claim 1, wherein said pharmaceutical composition further comprises a pharmaceutical carrier.

6. A method for treating hepatoma, which comprises administering an effective amount of the pharmaceutical composition to a subject afflicted with hepatoma:
    wherein the pharmaceutical composition comprises 5'-O-[(4-Cyanophenyl)methyl]-8-[[(3,4-dichlorophenyl) methyl]amino]-adenosine (VER-155008), 2-Phenyl-ethynesulfonamide (Pifithrin-μ), or pharmaceutical acceptable salts thereof.

7. The method for treating hepatoma according to claim 6, wherein said heat shock protein inhibitor is selected from a group consisting of VER-155008 and Pifithrin-μ.

8. The method for treating hepatoma according to claim 6, wherein said heat shock protein inhibitor is VER-155008.

9. The method for treating hepatoma according to claim 6, wherein said heat shock protein inhibitor is Pifithrin-μ.

10. The method for treating hepatoma according to claim 6, wherein said hepatoma is caused by hepatitis B virus.

* * * * *